(12) United States Patent
Asuke et al.

(10) Patent No.: US 7,305,868 B2
(45) Date of Patent: Dec. 11, 2007

(54) METHOD AND SYSTEM FOR EVALUATING LYOPHOBICITY OF INNER WALL OF FINE TUBE INCLUDING LYOPHOBIC FILM

(75) Inventors: Shintaro Asuke, Fujimi-machi (JP); Kazuo Higuchi, Suwa (JP)

(73) Assignee: Seiko Epson Corporation (JP)

( * ) Notice: Subject to any disclaimer, the term of this patent is extended or adjusted under 35 U.S.C. 154(b) by 382 days.

(21) Appl. No.: 11/085,030

(22) Filed: Mar. 18, 2005

(65) Prior Publication Data

US 2005/0214948 A1 Sep. 29, 2005

(30) Foreign Application Priority Data

Mar. 18, 2004 (JP) ............................ 2004-078265
Jun. 30, 2004 (JP) ............................ 2004-194177

(51) Int. Cl.
*G01N 13/00* (2006.01)
(52) U.S. Cl. .................................... 73/64.55; 73/61.43
(58) Field of Classification Search ............... 73/64.55, 73/61.43, 61.62, 53.01, 104; 422/68.1; 436/60
See application file for complete search history.

(56) References Cited

U.S. PATENT DOCUMENTS

| | | | | |
|---|---|---|---|---|
| 4,184,363 A | * | 1/1980 | Vassilev et al. ............ | 73/64.55 |
| 5,069,065 A | * | 12/1991 | Sprunt et al. .......... | 73/64.55 X |
| 6,154,283 A | * | 11/2000 | Shirasawa et al. .......... | 356/432 |
| 6,571,611 B2 | * | 6/2003 | Lacey et al. ............... | 73/61.62 |
| 6,604,054 B2 | * | 8/2003 | Lipscomb et al. ............ | 702/47 |
| 6,978,663 B1 | * | 12/2005 | Sinquefield ................ | 73/61.62 |
| 2002/0103352 A1 | * | 8/2002 | Sudor .................... | 73/61.62 X |
| 2004/0255650 A1 | * | 12/2004 | Moudgil et al. ........... | 73/64.55 |
| 2005/0160799 A1 | * | 7/2005 | Taylor ....................... | 73/61.62 |

FOREIGN PATENT DOCUMENTS

| | | | | | |
|---|---|---|---|---|---|
| JP | 60219514 A | * | 11/1985 | ................ | 73/64.55 |
| JP | 01174936 A | * | 7/1989 | ................ | 73/64.55 |
| JP | 02264830 A | * | 10/1990 | ................ | 73/64.55 |
| JP | 08050088 A | * | 2/1996 | | |
| JP | 08-334452 | | 12/1996 | | |
| JP | 09145588 A | * | 6/1997 | | |
| JP | 10206309 A | * | 8/1998 | | |
| JP | 2002116127 A | * | 4/2002 | | |
| JP | 2002122528 A | * | 4/2002 | | |
| SU | 1543298 A | * | 2/1990 | | |

* cited by examiner

*Primary Examiner*—Thomas P. Noland
(74) *Attorney, Agent, or Firm*—Harness, Dickey & Pierce, P.L.C.

(57) ABSTRACT

A method for evaluating lyophobicity of an inner wall of a fine tube having a lyophobic film formed on the inner wall includes a step of setting up a fine tube having a lyophobic film extending from an end of the inner wall of the fine tube to a predetermined position of the inner wall, in a liquid placed in a unit in such a manner that the lyophobic film is positioned uppermost and also includes a step of measuring the position of the liquid surface of the liquid that has risen in the fine tube and then stopped and then determining the position of the lower end of the lyophobic film.

14 Claims, 4 Drawing Sheets

METHOD AND SYSTEM FOR EVALUATING LYOPHOBICITY OF INNER WALL OF FINE TUBE INCLUDING LYOPHOBIC FILM

BACKGROUND OF THE INVENTION

1. Field of the Invention

The present invention relates to a method and system for evaluating lyophobicity of an inner wall of a fine tube including a lyophobic film formed on the inner wall.

2. Description of the Related Art

Japanese Unexamined Patent Application Publication No. 8-334452 (hereinafter referred to as Patent Document 1) discloses a method and system for evaluating lyophobicity of a wall of a fine channel, the wall being subjected to lyophobic treatment. In the evaluating method and system, a solution is fed into a fine tube in such a manner that an interface between the solution and air is formed, light or ultrasound is applied to the solution while the concentration or temperature of the solution is being continuously varied, and the reflection or the transmittance is then measured. That is, in the procedure, lyophobic treatment to which the inner wall of the fine tube is subjected is evaluated based on a point of time when the air-solution interface, of which the shape is continuously varied, becomes flat.

According to Patent Document 1, lyophobicity of the entire inner wall is evaluated; hence, the method and system cannot be used to evaluate the lyophobicity of an inner wall having a boundary between lyophobic portion and a lyophilic portion at a specific position of the inner wall. Furthermore, no information about the position of the boundary can be obtained.

SUMMARY OF THE INVENTION

The present invention has been made to solve the above problems. It is an object of the present invention to provide a method and system for evaluating lyophobicity of an inner wall of a nozzle, in which the position of the boundary between a lyophobic area and an untreated area (lyophilic area) of the inside of a nozzle partially having a film can be determined.

The present invention provides a method for evaluating lyophobicity of an inner wall of a fine tube having a lyophobic film formed on the inner wall. The method includes a step of setting up a fine tube, having a lyophobic film extending from an end of the inner wall of the fine tube to a predetermined position of the inner wall, in a liquid placed in a control unit in such a manner that the lyophobic film is positioned uppermost and also includes a step of measuring the position of the surface of the liquid that has risen in the fine tube and then stopped to determine the position of the lower end of the lyophobic film. By the method, the position of the lower end of a lyophobic film formed in a fine tube can be determined, so that the method is applicable to various types of tube in which capillary action occurs. Since dispensing nozzles and other nozzles can be improved in ability of liquid repellency of a discharged liquid by forming lyophobic films on end regions of the inner walls of the nozzles, the method is useful in evaluating the discharging stability of each nozzle.

In the method, the pressure, temperature, and humidity in the control unit are preferably controlled to be constant. Therefore, the liquid level rising, due to capillary action, in the fine tube can be controlled to be constant and the position of the lower end of the lyophobic film can be specified under a constant condition. The method can be used to evaluate the lyophobicity of various types of lyophobic film by varying the pressure, the temperature, and the humidity.

In the method, the pressure, temperature, and humidity in the fine tube are preferably controlled to be constant. Therefore, the liquid level rising, due to capillary action, in the fine tube can be controlled to be constant and the position of the lower end of the lyophobic film can be specified under a constant condition. The method can be used to evaluate lyophobicity of various types of lyophobic film by varying the pressure, the temperature, and the humidity.

In the method, the liquid preferably contains one selected from the group consisting of pure water, cyclohexylbenzene, diiodomethane, bromonaphthalene, ethylene glycol, hexane, octane, decane, and glycerin, depending on the type and lyophobicity of the lyophobic film. That is, an optimum component of the liquid can be selected depending on the type and lyophobicity of the lyophobic film, for example, the nature whether the lyophobic film is oil-repellent or water-repellent. Therefore, the method can be used to evaluate the lyophobicity of various types of lyophobic film by varying the type of liquid.

In the method, the level of the liquid in the fine tube is preferably measured at a center zone of a liquid surface in the fine tube. Therefore, the position of the lower end of the lyophobic film formed on the inner wall of the fine tube can be precisely measured.

In the method, a plurality of spots are set on a liquid surface in the fine tube, the shape of the meniscus of the liquid surface is specified using the spots, and then, the position of the lower end of the lyophobic film is preferably determined based on the specified shape of meniscus. Therefore, the position of the lower end of the lyophobic film formed on the inner wall of the fine tube can be precisely measured, so that the method is applicable to various types of tube in which capillary action occurs.

In the method, the fine tube is preferably a type of dispensing nozzle or inkjet nozzle. Therefore, the method can be used to quantitatively evaluate the lyophobicity of the inner wall of such a nozzle, the inner wall being subjected to lyophobic treatment.

The present invention provides another method for evaluating lyophobicity of the inner walls of fine tubes having lyophobic film formed on the inner walls. This method includes a step of stting up a plurality of fine tubes, each having a lyophobic film extending from an end of the inner wall of a corresponding fine tube to predetermined position of the inner wall, in a liquid placed in a control unit in such a manner that the lyophobic films are positioned uppermost and also a step of measuring the positions of the surfaces of the liquid that have risen in the fine tubes and then stopped to determine the positions of the lower ends of the lyophobic films. This method is useful in continuously inspecting a large number of fine tubes at high speed and can be used to evaluate various types of tube in which capillary action occurs. Since dispensing nozzles and other nozzles can be improved in ability of liquid repellency of a discharged liquid by forming lyophobic films on end regions of the inner walls of the nozzles, the method is useful in evaluating the discharging stability of the nozzles.

In this method, the pressure, temperature, and humidity in the control unit are preferably controlled to be constant. Therefore, the liquid levels rising, due to capillary action, in the fine tubes can be controlled to be constant and the positions of the lower ends of the lyophobic films can be specified under a constant condition. The method can be used to evaluate the lyophobicity of various types of lyophobic film by varying the pressure, the temperature, and the humidity.

In this method, the pressure, temperature, and humidity in the fine tubes are preferably controlled to be constant. Therefore, the liquid levels rising, due to capillary action, in the fine tubes can be controlled to be constant and the positions of the lower ends of the lyophobic films can be specified under a constant condition. The method can be used to evaluate lyophobicity of various types of lyophobic film by varying the pressure, the temperature, and the humidity.

In this method, the liquid preferably contains one selected from the group consisting of pure water, cyclohexylbenzene, diiodomethane, bromonaphthalene, ethylene glycol, hexane, octane, decane, and glycerin, depending on the type and lyophobicity of the lyophobic film. That is, an optimum component of the liquid can be selected depending on the type and lyophobicity of the lyophobic film, for example, the nature whether the lyophobic films are oil-repellent or water-repellent. Therefore, the method can be used to evaluate the lyophobicity of various types of lyophobic film by varying the type of liquid.

In this method, the levels of the liquid in the fine tubes are preferably measured at center zones of liquid surfaces in the fine tubes. Therefore, the positions of the lower ends of the lyophobic films formed on the inner walls of the fine tubes can be precisely measured.

In this method, a plurality of spots are set on liquid surfaces in the fine tubes, the shape of the meniscus of the liquid surface is specified using the spots, and then, the positions of the lower ends of the lyophobic films are preferably determined based on the specified shape of meniscus. Therefore, the positions of the lower ends of the lyophobic films formed on the inner walls of the fine tubes can be precisely measured, so that the method is applicable to various types of tube in which capillary action occurs.

In this method, the fine tubes are preferably a type of dispensing nozzle or inkjet nozzle. Therefore, the method can be used to quantitatively evaluate the lyophobicity of the inner walls of nozzles, the inner walls being subjected to lyophobic treatment.

The present invention provides a system for evaluating lyophobicity of inner walls of a plurality of fine tubes having lyophobic films formed on the inner walls. The system includes a control unit inside which pressure, temperature, and humidity are controlled to keep a constant ambience; a fixture for setting up and fixing a plurality of fine tubes each having a lyophobic film extending from an end of the inner wall of the fine tube to a predetermined position of the inner wall, in such a manner that the lyophobic films are positioned uppermost, the fixture being vertically movable; a tank for containing a liquid in which the fine tubes fixed to the fixture are partly immersed; and a level sensor for measuring the positions of the liquid surfaces that have risen in the fine tubes and then stopped near the lower ends of the lyophobic films, the level sensor being capable of moving horizontally. The fixture, the tank, and the level sensor are placed in the control unit and the positions of the lower ends of the lyophobic films are determined by measuring the positions of the liquid surfaces. The system is useful in inspecting a large number of fine tubes at high speed to determine the positions of the lower ends of lyophobic films formed on the inner walls of the fine tubes. Furthermore, the system can be used to inspect various types of fine tube in which capillary action occurs. Since dispensing nozzles and other nozzles can be improved in ability of liquid repellency of a discharged liquid by forming lyophobic films on end regions of the inner walls of the nozzles, the system is useful in evaluating the discharging stability of the nozzles.

DESCRIPTION OF THE PREFERRED EMBODIMENTS

Figure 1:
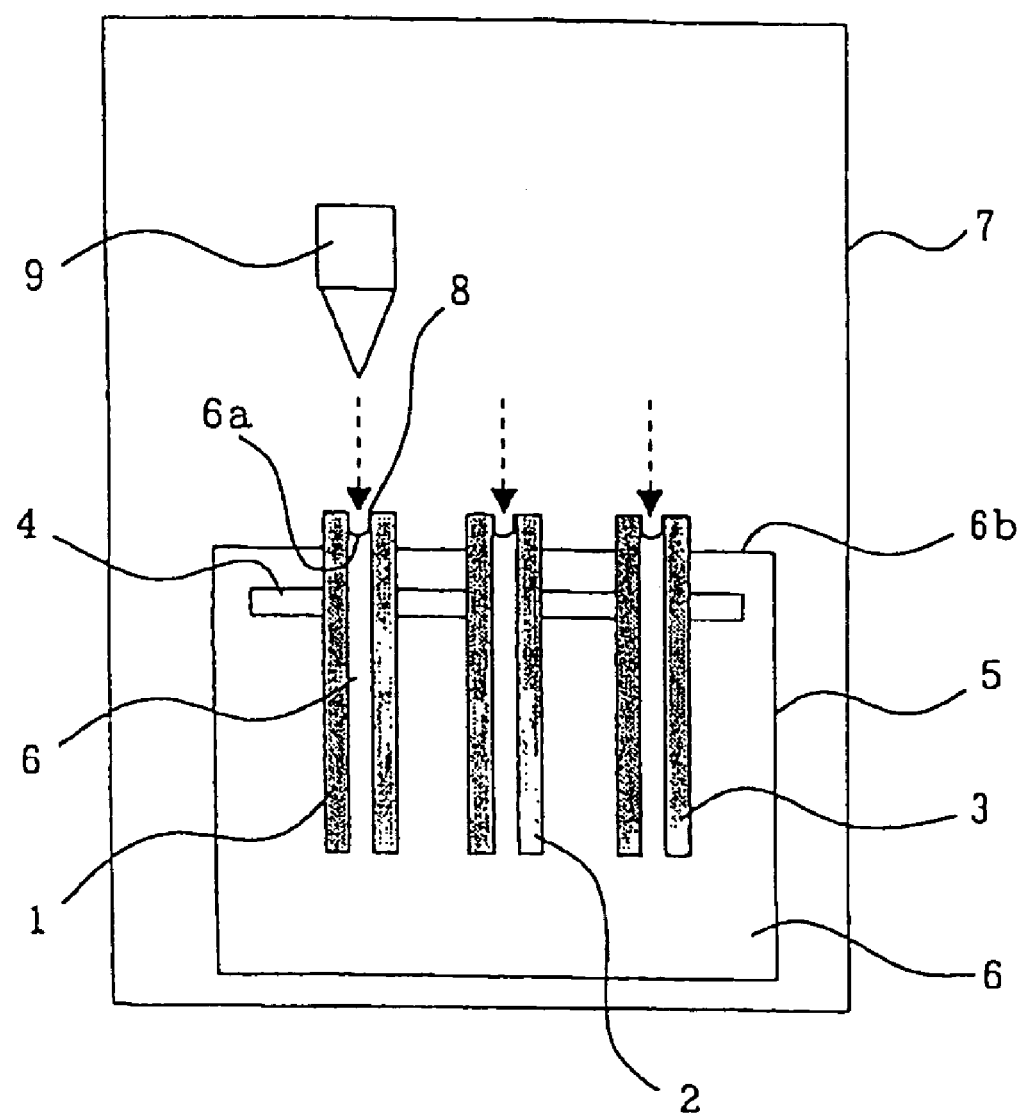
FIG. 1 is an illustration showing a method and system, according to an embodiment of the present invention, for evaluating lyophobicity of an inner wall of a nozzle.
Figure 2:
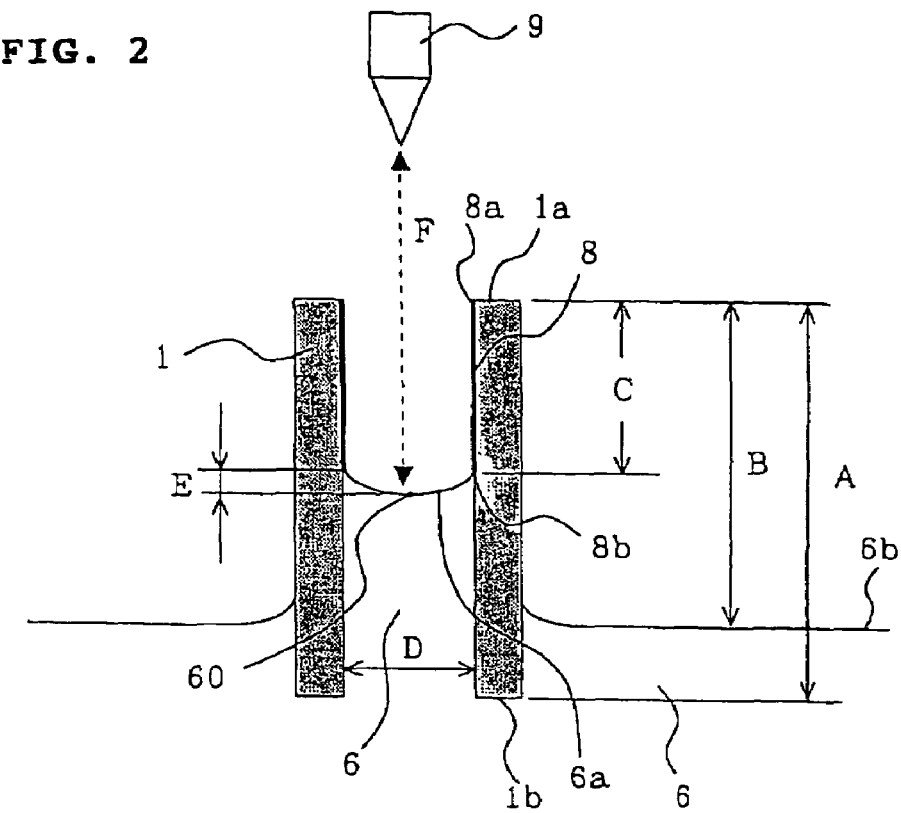
FIG. 2 is an enlarged view of a principal part of FIG. 1.

FIG. 1 is an illustration showing a method and a system, according to an embodiment of the present invention, for evaluating lyophobicity of an inner wall of a nozzle having a lyophobic film formed on the inner wall. FIG. 2 is an enlarged view of a principal part of FIG. 1. The method and the system are used to evaluate a state of lyophobic treatment on an inner wall of a nozzle of a dispensing unit or an inkjet unit used to manufacture, for example, electronic devices such as display units and semiconductor devices, that is, the method and the system are used to quantitatively evaluate a boundary between a lyophobic portion and an lyophilic portion. In particular, the method and the system are useful in determining the position of the boundary between a hydrophobic area and an untreated area (hydrophilic area) on the inner wall.

With reference to FIG. 1, a first dispensing nozzle 1, a second dispensing nozzle 2, and a third dispensing nozzle 3 respectively having corresponding lyophobic treated areas formed on the inner walls thereof are fitted to a fixture 4, in such a manner that they are set up at constant intervals and the lyophobic treated areas are positioned uppermost. The first, second, and third dispensing nozzle 1, 2, and 3 can be immersed in pure water as a liquid 6 stored in a tank 5, by vertically moving the fixture 4.

The tank 5, the liquid 6, the fixture 4, and the first, second., and third dispensing nozzle 1, 2, and 3 are placed in a control unit 7. The pressure, temperature, and humidity inside the control unit 7 are controlled to keep a constant ambience, whereby the levels of the liquid 6 rising due to capillary action in the first, second, and third dispensing nozzle 1, 2, and 3 are maintained constant.

The fixture 4 is immersed in the liquid 6 stored in the tank 5, and the first, second, and third dispensing nozzle 1, 2, and 3 fitted to the fixture 4 are also immersed in the liquid 6 except their upper portions where lyophobic films 8 (lyophobic treated areas) are formed on the inner walls. In this situation, the surfaces 6a of the liquid 6 in the first, second, and third dispensing nozzle 1, 2, and 3 are higher than the surface 6b of the liquid 6 in the tank 5 because of capillary action.

A component of the liquid 6 can be selected depending on the type and lyophobicity of the lyophobic films 8. In this embodiment, the liquid 6 is pure water. When the lyophobic films 8 are oil-repellent or water-repellent, the liquid 6 may be one selected from the group consisting of cyclohexylbenzene, diiodomethane, bromonaphthalene, ethylene glycol, hexane, octane, decane, and glycerin.

With reference to FIG. 2, the lyophobic film 8 of the first dispensing nozzle 1 is formed on an end portion of the inner wall of the first dispensing nozzle 1 and extends from the upper end 1a of the first dispensing nozzle 1 to a position spaced from the upper end 1a at a predetermined distance. This lyophobic film 8 can be formed by subjecting the end portion to lyophilic treatment. The liquid 6 comes in contact with the boundary between a lyophobic portion and a lyophilic portion of the first dispensing nozzle 1 because the level of the liquid 6 in the first dispensing nozzle 1 rises due to capillary action. A liquid surface 6a in the first dispensing nozzle 1 forms a concave interface (meniscus) due to the surface tension.

With reference to FIG. 2, symbol A represents the length of the first dispensing nozzle 1, symbol D represents the inner diameter of the first dispensing nozzle 1, symbol B represents the distance between a liquid surface 6b in the tank 5 and the upper end 1a of the first dispensing nozzle 1 partly immersed in the liquid 6, and symbol C represents the length of the lyophobic film 8 of the first dispensing nozzle 1 from the upper end 8a of the lyophobic film 8 to the lower end 8b thereof. A center zone 60 of the liquid surface 6a is located below the lower end 8b of the lyophobic film 8, the distance between the center zone 60 and the lower end 8b being represented by symbol E.

A non-contact level sensor 9, for example, a laser displacement gauge for micro-spots, is placed above the first dispensing nozzle 1 and used to measure the distance between the tip of the level sensor 9 and the center zone 60 of the liquid surface 6a in the first dispensing nozzle 1. Though the center zone 60 of the liquid surface 6a is a measurement object of the level sensor 9, the position of the lyophobic film 8 of the first dispensing nozzle 1 is specified based on the shape of the meniscus of the liquid surface 6a and the length of an immersed portion of the first dispensing nozzle 1, the immersed portion being located under the liquid surface 6b in the tank 5, the length of the immersed portion being represented by the formula A-B. The shape of the meniscus can be identified by measuring a large number of spots on the meniscus at a pitch of several micrometers and is used to calculate the offset between the center zone 60 of the liquid surface 6a and the boundary between a lyophobic area and lyophilic area of the inner wall of the first dispensing nozzle 1.

The operation of the embodiment having the above configuration will now be described.

Figure 3:
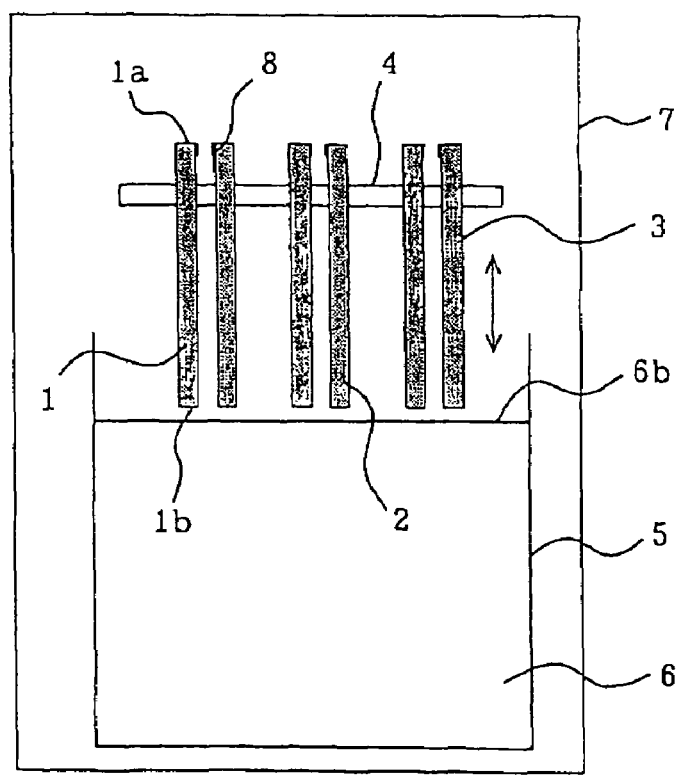
FIG. 3 is an illustration showing an operation in the embodiment of the present invention.

With reference to FIG. 3, in the control unit 7, the pressure, temperature, and humidity are controlled to be constant. A component of the liquid 6 is selected depending on the type and lyophobicity of the lyophobic films 8. The first, second, and third dispensing nozzle 1, 2, and 3 are fitted to the fixture 4 in such a manner that the lyophobic films 8 are positioned uppermost and the first, second, and third dispensing nozzle 1, 2, and 3 are set up at the same level. The first, second, and third dispensing nozzle 1, 2, and 3 and the fixture 4 are then moved downward.

Figure 4:
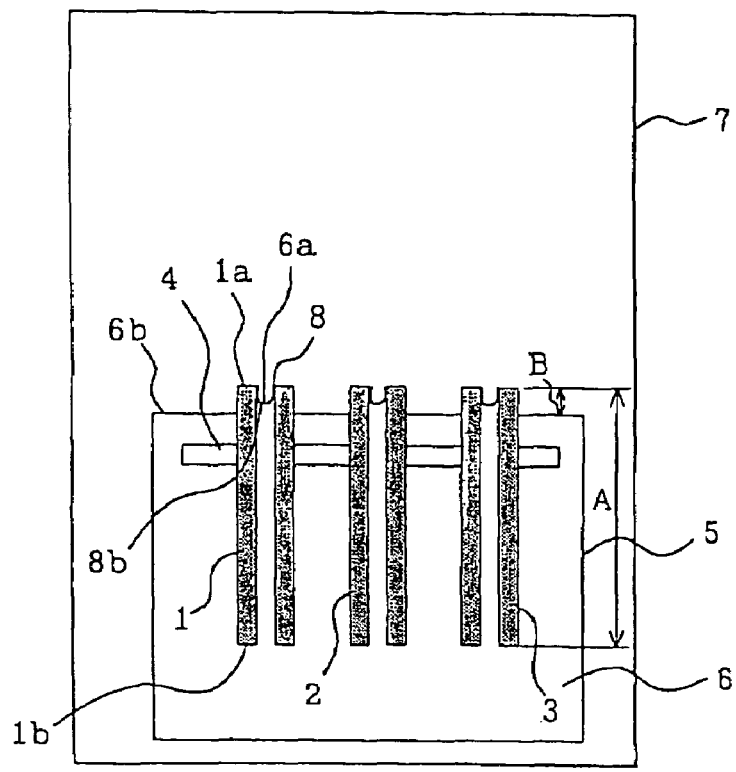
FIG. 4 is an illustration showing an operation in the embodiment.
Figure 5:
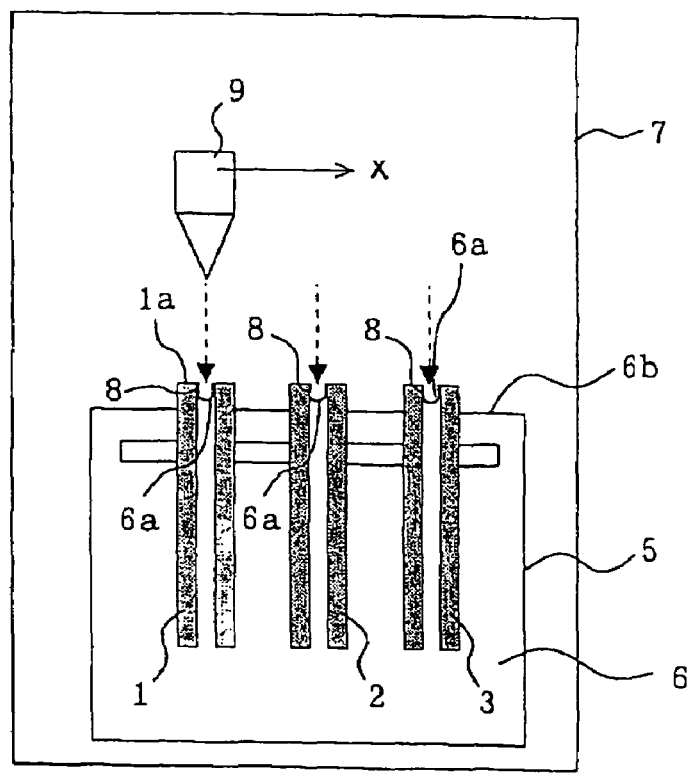
FIG. 5 is an illustration showing an operation in the embodiment.

The first, second, and third dispensing nozzles 1, 2, and 3 are immersed from their lower ends into the liquid 6 until the lower ends of the nozzles reach a depth represented by the formula A-B. The lower ends are then maintained at the position as shown in FIG. 4. The immersion depth represented by the formula A-B is determined in advance by calculating a level of the liquid 6 that rises in the first, second, and third dispensing nozzle 1, 2, and 3 and stops at a lower end 8b of the lyophobic film 8. If length A and distance B are known, the levels of the liquid surfaces 6a can be determined. Therefore, the length of immersed portions of the first, second, and third dispensing nozzle 1, 2, and 3 can be determined. Since the liquid 6 is uniform, the length of the immersed portions can be determined.

Figure 7:
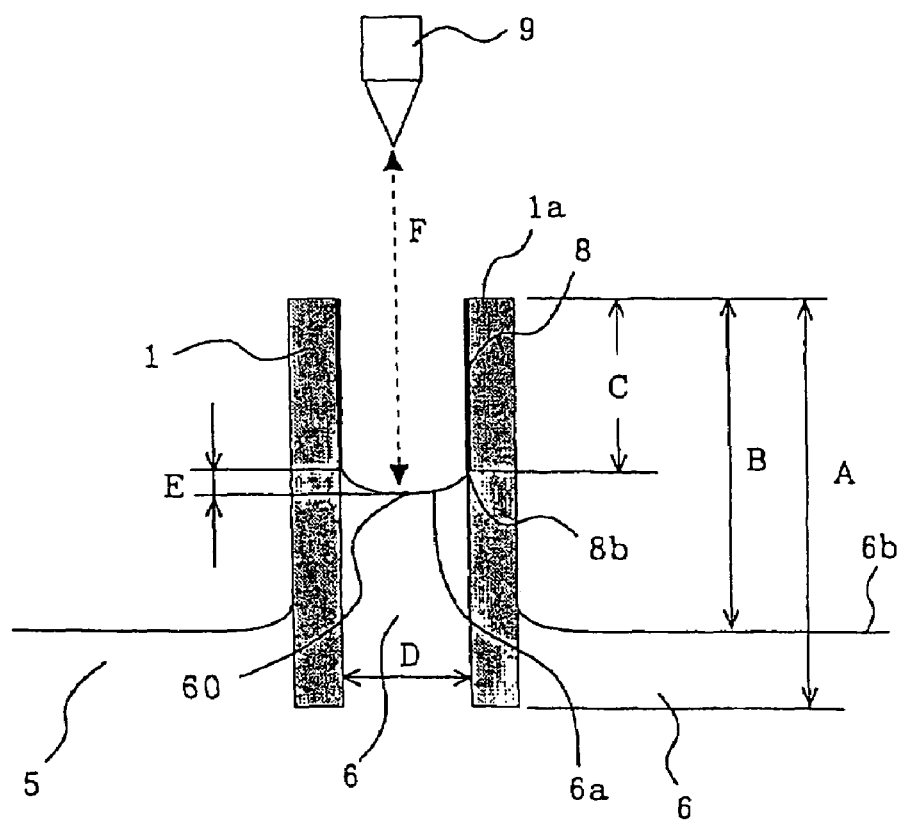
FIG. 7 is an enlarged view of a principal part of FIG. 5.

Since the liquid 6 rises in the first, second, and third dispensing nozzle 1, 2, and 3 and the lyophobic film 8 extend to predetermined positions in the first, second, and third dispensing nozzle 1, 2, and 3, the liquid 6 reaches the lower ends 8b of the lyophobic films B to form concave menisci on the liquid surfaces 6b as shown in FIG. 7.

In this situation, the non-contact type level sensor 9 such as a laser displacement gauge for micro spots is moved along a liquid surface 6b in the tank 5 in the direction represented by symbol X. The level sensor 9 is allowed to stop directly above the first dispensing nozzle 1 and then used to measure the distance F between the tip of the level sensor 9 and the center zone 60 of the liquid surface 6a in the first dispensing nozzle 1 as shown in FIG. 7. The distance F is corrected with a correction formula using the immersion depth represented by the formula A-B, the shape of the meniscus of the liquid surface 6a in the nozzle, and the like, whereby the distance E (correction distance) between the center zone 60 of the liquid surface 6a and the lower end 8b of the lyophobic film 8 of the first dispensing nozzle 1 is determined. That is, a large number of spots on the liquid surface 6a are measured at a pitch of several micrometers, whereby the shape of the meniscus is specified. The offset from the center zone 60 to the position of the liquid at the boundary is calculated based on the shape of the meniscus, whereby the position of the lyophobic film 8 is specified. Since inside of the control unit 7 is maintained at a constant pressure, temperature, and humidity, the liquid 6 is also maintained at the same conditions. Therefore, if the distance F between the tip of the level sensor 9 and the center zone 60 of the liquid surface 6a in each nozzle is measured, the actual distance F-E between the lower end 8b of each lyophobic film 8 and the tip of the level sensor 9 can be obtained using the same correction formula.

After the measurement of the first dispensing nozzle 1 is finished, the level sensor 9 is moved in direction X and the liquid surface 6a in the second dispensing nozzle 2 is then measured. The level sensor 9 is further moved in direction X and the liquid surface 6a in the third dispensing nozzle 3 is then measured. In this procedure, the positions of the lyophobic film 8 of the second and third dispensing nozzles 2 and 3 are determined by the same calculation as described above. If the position of any one of the lyophobic films 8 is displaced from a standard position, this lyophobic film 8 is judged to be abnormal.

Figure 6:
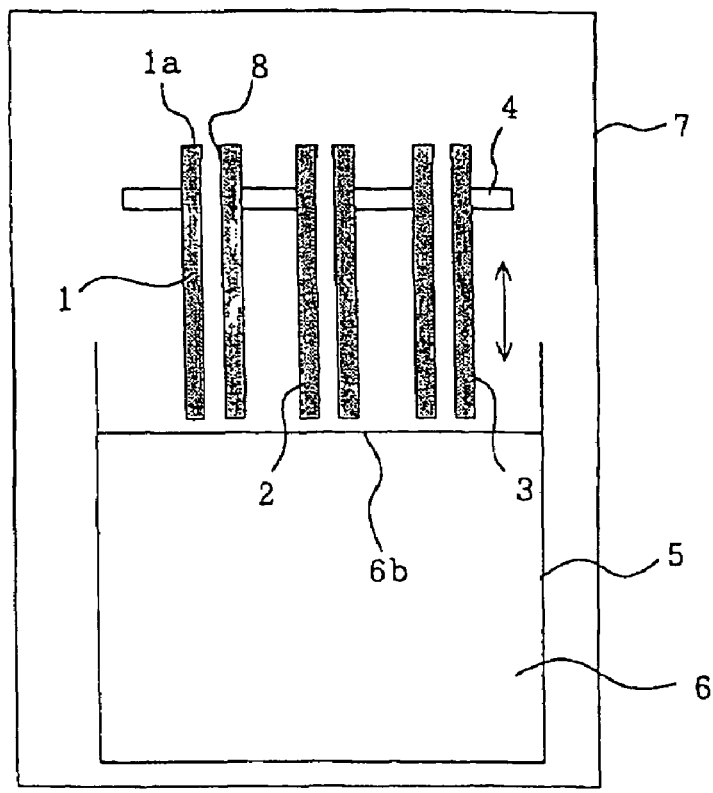
FIG. 6 is an illustration showing an operation in the embodiment.

After the above operation is finished, the fixture 4 is moved upward, whereby the first, second, and third dispensing nozzle 1, 2, and 3 are withdrawn from the liquid 6 as shown in FIG. 6.

The resulting first, second, and third dispensing nozzle 1, 2, and 3 are replaced with other nozzles and the operations shown in FIGS. 3 to 6 are then repeated.

The method and system of the present invention can be applied to evaluate a nozzle plate having a large number of fine channels.

As described above, in this embodiment, the levels of the liquid 6 rising, due to capillary action, in the first, second, and third dispensing nozzle 1, 2, and 3 are measured in a constant condition; hence, the boundary between the lyophobic area and the lyophilic area can be specified, whereby the positions of the lower ends of the lyophobic films 8 can be measured. Therefore, according to the present invention, a large number of fine tubes can be continuously inspected at high speed and various types of lyophobic film and lyophobicity thereof can be evaluated by varying the pressure, the temperature, the humidity, and the type of liquid. Various types of tube in which capillary action occurs can be evaluated. Since dispensing nozzles and inkjet nozzles can be improved in ability to repel a discharged liquid by forming lyophobic films on end regions of the inner walls of the nozzles, the method and system of the present invention are useful in evaluating the discharging stability of the nozzles.

EXAMPLE

Inside of a control unit 7 for controlling pressure, temperature, and humidity was controlled to maintain a constant ambience at a pressure of 90,000 Pa, a temperature of 25° C., and a relative humidity of 45%. Three dispensing nozzles 1 to 3, each of which has a fine channel with a inner diameter D of 30 µm partly treated to be hydrophobic with a coating agent (Optool DSX manufactured by Daikin Industries, Ltd.) to form a lyophobic film 8 on the inner wall of the channel, were fixed to a fixture 4 in such a manner that the dispensing nozzles 1, 2, and 3 were set up at constant intervals and the lyophobic films 8 were positioned uppermost as shown in FIG. 7. The resulting fixture 4 was moved downward toward a tank 5 containing pure water 6, whereby the dispensing nozzles 1, 2, and 3 were immersed from lower ends in the pure water 6 until the lower ends reached a predetermined depth.

The pure water 6 rose in the dispensing nozzles 1, 2, and 3 up to the lower ends 8b of the lyophobic films 8. A center zone 60 of the liquid surface 6a of the pure water 6 in each nozzle was measured with a laser displacement gauge 9 for micro-spots. The measurement showed that the pure water 6 rose up to a position 68 µm below the top of each nozzle.

A large number of spots on the liquid surface 6a of the pure water 6 in each nozzle were measured at a pitch of several micrometers, whereby the shape of the meniscus of the pure water 6 in each nozzle was specified. From the meniscus shape, the offset from the center zone 60 of the liquid surface 6a in each nozzle to the position of the pure water 6 at the boundary of the lyophobic film was calculated to be 8 µm. The distance between the top 8a of each nozzle and the lower end 8b of each lyophobic film 8 was then calculated to be 60 µm according to the following equation: 68 µm−8 µm=60 µm. The length of immersed portions of the dispensing nozzles 1, 2, and 3 was also taken into consideration in this calculation.

The entire disclosures of Japanese Patent Application Nos. 2004-078265 filed Mar. 18, 2004 and 2004-194177 filed Jun. 30, 2004 are hereby incorporated by reference.

What is claimed is:

1. A method for evaluating lyophobicity of a lyophobic film formed on an inner wall of a fine tube, comprising:
   a step of setting up a fine tube, having a lyophobic film extending from an end of the inner wall of the fine tube to a predetermined position of the inner wall, in a liquid placed in such a manner that the lyophobic film is positioned uppermost; and
   a step of measuring the position of the surface of the liquid that has risen in the fine tube and then stopped to determine the position of the boundary of the lyophobic film.

2. The method according to claim 1, wherein the pressure, temperature, and humidity in all processing atmosphere are controlled to keep a constant ambience.

3. The method according to claim 1, wherein the pressure, temperature, and humidity in the fine tube are controlled to keep a constant ambience.

4. The method according to claim 1, wherein the liquid contains one selected from the group consisting of pure water, cyclohexylbenzene, diiodomethane, bromonaphthalene, ethylene glycol, hexane, octane, decane, and glycerin, depending on the type and lyophobicity of the lyophobic film.

5. The method according to claim 1, wherein the level of the liquid in the fine tube is measured at the center zone of the liquid surface in the fine tube.

6. The method according to claim 1, wherein a plurality of spots are set on the liquid surface in the fine tube, the shape of the meniscus of the liquid surface in the fine tube is specified using the spots, and then, the position of the boundary of the lyophobic film formed in the fine tube is determined based on the specified shape of the meniscus.

7. The method according to claim 1, wherein the fine tube is a type of dispensing nozzle or inkjet nozzle.

8. A method for evaluating lyophobicity of lyophobic films formed on the inner walls of fine tubes, comprising:
   a step of setting up a plurality of fine tubes, each having a lyophobic film extending from an end of the inner wall of a corresponding fine tube to predetermined position of the inner wall, in a liquid placed in such a manner that the lyophobic film of each fine tube is positioned uppermost; and
   a step of measuring the positions of the surfaces of the liquid that have risen in the fine tubes and then stopped, to determine the position of the boundary of the lyophobic film of each fine tube.

9. The method according to claim 8, wherein the pressure, temperature, and humidity in all processing atmosphere are controlled to keep a constant ambience.

10. The method according to claim 8, wherein the pressure, temperature, and humidity in each fine tube are controlled to keep a constant ambience.

11. The method according to claim 8, wherein the liquid contains one selected from the group consisting of pure water, cyclohexylbenzene, diiodomethane, bromonaphthalene, ethylene glycol, hexane, octane, decane, and glycerin, depending on the type and lyophobicity of the lyophobic film.

12. The method according to claim 8, wherein the level of the liquid in each fine tube is measured at the center zone of the liquid surface in each fine tube.

13. The method according to claim 8, wherein a plurality of spots are set on the liquid surface in each fine tube, the shape of the meniscus of the liquid surface in each fine tube is specified using the spots, and then, the position of the boundary of the lyophobic film formed in each fine tube is determined based on the specified shape of the meniscus.

14. The method according to claim 8, wherein each fine tube is a type of dispensing nozzle or inkjet nozzle.

* * * * *